United States Patent [19]

Scott

[11] Patent Number: 5,174,872
[45] Date of Patent: Dec. 29, 1992

[54] METAL-FREE BUFFER FOR ION SELECTIVE ELECTRODE-BASED ASSAYS

[75] Inventor: William J. Scott, Peekskill, N.Y.

[73] Assignee: Technicon Instruments Corporation, Tarrytown, N.Y.

[21] Appl. No.: 535,631

[22] Filed: Jun. 8, 1990

[51] Int. Cl.[5] ........................................ G01N 27/333
[52] U.S. Cl. .............................. 204/153.1; 204/153.13; 204/153.15; 204/416; 204/418; 436/18; 436/68; 436/74; 436/79; 436/125
[58] Field of Search ................... 436/18, 68, 74, 79, 436/124, 125; 204/153.13, 153.15, 153.17

[56] References Cited

U.S. PATENT DOCUMENTS

| | | | |
|---|---|---|---|
| 2,359,052 | 7/1940 | Scharer | 436/18 X |
| 4,193,766 | 3/1980 | Daunora et al. | 436/18 X |
| 4,214,968 | 7/1980 | Battaglia et al. | 204/418 |
| 4,248,634 | 2/1981 | Forester | 436/18 X |
| 4,361,473 | 11/1982 | Young et al. | 204/418 |
| 4,555,348 | 11/1985 | Moran | 436/18 X |
| 4,704,365 | 11/1987 | Yost | 436/18 |
| 4,810,351 | 3/1989 | Chapoteau et al. | 204/418 |
| 4,824,551 | 4/1989 | Rupich | 204/431 |
| 4,846,937 | 7/1989 | Driscoll et al. | 204/153.17 |
| 4,877,492 | 10/1989 | Uematsu et al. | 436/79 X |

OTHER PUBLICATIONS

"Handbook of Chemistry and Physics", 52nd Edition, p. D-104, (1971).
J. Bagg, Anal. Chem., vol. 48, No. 12, pp. 1811-1812, Oct. 1976.

*Primary Examiner*—T. Tung
*Attorney, Agent, or Firm*—Jeffrey M. Greenman; Roger Norman Coe

[57] ABSTRACT

A heavy metal-free composition and its method of use in an ion selective electrode-based assay are disclosed. The heavy metal-free composition includes a borate compound and an alkalinity adjusting compound, and is used to dilute a test sample; buffer the test sample; and substantially reduce the effects of interferents present in the test sample on the ion selective electrode-based assay. The heavy metal-free composition and its method of use are especially useful in an ion selective electrode-based assay for carbonate ion concentration in a test sample, like blood serum, blood plasma, urine or cerebrospinal fluid.

31 Claims, 3 Drawing Sheets

METAL-FREE BUFFER FOR ION SELECTIVE ELECTRODE-BASED ASSAYS

FIELD OF THE INVENTION

The present invention relates to an assay of a test sample, such as a biological fluid, like blood plasma, blood serum or urine, for the presence or concentration of a predetermined analyte, like carbonate ion, by an ion selective electrode. More particularly, the present invention relates to an ion selective electrode-based assay of a test sample for a predetermined analyte, wherein a heavy metal-free composition, including a buffer compound, like a borate compound, is used to dilute the test sample, to buffer the test sample within a suitable pH range and to substantially reduce the effects of interferents present in the test sample on the assay. The prior art compositions used to dilute and buffer the test sample include a complex of a heavy metal ion to reduce the effects of interferents present in the test sample on the assay. Surprisingly and unexpectedly, the heavy metal-free composition of the present invention provides accurate and sensitive ion selective electrode-based assays for a predetermined analyte, and substantially reduces the effects of interferents without using potentially-toxic heavy metal complexes, like mercury complexes. In addition to reducing the effects of interferents, the heavy metal-free composition maintains electrode selectivity, maintains electrode lifetime, and produces a significantly less-toxic waste product. Accordingly, disposal of the spent, heavy metal-free composition is facilitated.

BACKGROUND OF THE INVENTION

Several methods are available to assay for the presence or concentration of a predetermined analyte, like an ion, in a test sample. These materials include wet phase and dry phase colorimetric assays, and assays based on flame photometry, atomic absorption photometry, ion selective electrodes and multiple liquid phase partitioning. Recently, the ion selective electrode method of analysis has been more widely used, especially in regard to automated systems, as improvements in ion selective electrodes have developed. In particular, ion selective electrodes now have sufficient selectivity, sensitivity and operating lifetimes to be useful in automated systems.

One important aspect of an ion selective electrode is the use of particular compounds or compositions that preferentially or selectively complex with, and therefore isolate, a predetermined analyte, usually an ion, from a test sample. These compounds, known as ionophores, have the capability of selectively isolating a predetermined ion from its counterion and from other ions in the test sample, thereby causing a charge separation and a corresponding change in electrical conductivity in the phase containing the ionophore.

Ion selective electrodes therefore have been used to assay a test sample for the presence or concentration of a predetermined ion, either anionic or cationic, in solution. The prior art describes a variety of ion selective electrode types and structures to detect or measure a particular predetermined ion in solution. In general, devices that detect or measure the presence or concentration of a predetermined ion include a reference electrode and an electrode that responds preferentially or specifically to the predetermined ion in the test sample. When the reference electrode and the ion selective electrode each are immersed in solutions including differing concentrations of the predetermined ion, an electrical potential is generated in the electrochemical cell. This electrical potential is measured, and is correlated to the concentration of the predetermined analyte in the test sample.

In particular, when two solutions having unequal concentrations of the predetermined ion are separated by an electrically conductive membrane, an electromotive force (EMF) is generated. The EMF developed by the electrochemical cell is a function of the concentration, or the ionic activity, of the solutions on either side of the membrane. This phenomenon is expressed mathematically by the Nernst Equation (1):

$$E = \frac{RT}{nF} \ln \frac{(a_2)}{(a_1)}, \qquad (1)$$

wherein E is the EMF of the particular electrochemical cell, F is the Faraday constant, R is the gas constant, T is the temperature in °K. (degrees Kelvin) and $a_1$ and $a_2$ are the activities of the predetermined ion in solution. The subscript 1 denotes the solution on one side of the membrane; the subscript 2 denotes the solution on the other side of the membrane The electrical charge of the predetermined ion is denoted by n.

The measurement is a differential potentiometric measurement of potential differences arising between the two identical electrochemical half-cells that are immersed in solutions of different activity and are separated by a salt bridge or a membrane. The two half-cells together comprise a concentration cell In the present case, the activity of one half-cell ($a_1$) is fixed (reference), whereas the activity of the other half-cell ($a_2$) (sample) is variable, such that the EMF of the concentration cell is defined from the Nernst equation (Eq. 1).

In such electrochemical concentration cells, the membrane can be a simple fritted glass barrier that allows a small, but measurable, degree of ion diffusion from one solution to the other solution on the opposite side of the membrane. Alternatively, a nonporous, electrically-nonconductive membrane, such as polyvinyl chloride, impregnated with an ionophore can be employed. In the absence of the ionophore, the membrane is an insulator and no EMF can be measured. When an ionophore is incorporated into the membrane, charged ions are bound to the membrane and a small, measurable current can be induced to flow. Such cells are ion selective because the ionophore preferentially or selectively binds to, or complexes with, the predetermined ion. Thus, the ionophore binds essentially only to the predetermined ion and any measurable EMF is due solely to the presence of the predetermined ion.

For example, it is known that certain antibiotics, such as valinomycin, have an effect on the electrical properties of phospholipid bilayer membranes (biological membranes). These antibiotics solubilize cations within the membrane in the form of mobile charged complexes, thereby providing a "carrier" mechanism whereby cations can cross the insulating hydrophobic interior of the membrane. These cation-antibiotic complexes have the sole purpose of carrying the charge of the complex through the hydrophobic membrane. In an ion selective electrode (ISE), the cation-antibiotic complexes generate a measurable voltage differential between the solutions on either side of the ISE membrane.

Therefore, a concentration cell for determining potassium ion concentration in a test sample results from using an ionophore, e.g. valinomycin, that is specific for potassium ion ($K^+$). In the presence of potassium ions, valinomycin incorporated into a suitable membrane produces a concentration gradient across the membrane by binding and transporting the potassium ion, thus generating an electric potential across the membrane. A known, reference concentration of potassium ion contacts one side of the membrane and the test sample contacts the other. The resulting EMF is measured using external reference electrodes, and the measured EMF is used to calculate the unknown concentration of potassium ions in the test sample from equation (1). Because essentially only potassium ion binds to the valinomycin present in the membrane, the conductive path only appears for potassium ions. Therefore, the measured EMF is attributable solely to the potassium ion concentration gradient across the membrane. The actual current flowing across the membrane is so small that no significant quantity of potassium ion or counterion is transported through the membrane. Electrical neutrality of the membrane is maintained either by a reverse flow of hydrogen ions (protons), or by a parallel flow of hydroxyl ions.

This differential measurement technique has been used to measure the concentration or activity of constituents of biological fluids, such as hydrogen ion ($H^+$), sodium ($Na^+$), potassium ($K^+$), calcium ($Ca^{++}$) and chloride ($Cl^-$). In addition, this technique often employs biosensors or enzyme electrodes that include a biological catalyst (e.g., immobilized enzymes, cells, or layers of tissues) coupled to an electrode and are sensitive to a product or cosubstrate of the biologically catalyzed reaction. Accordingly, the concentration of an enzyme or of a substrate can be determined using differential measurement techniques.

In the past, an ISE generally comprised an electrode body, usually a type of glass container containing a reference solution of known ion concentration in contact with a half-cell of known potential, generally written as Ag/AgCl/"XMCl"; and an ion selective glass membrane mounted in an aperture in the electrode body such that, when the electrode was immersed in the solution including an unknown concentration of the ion, the glass membrane contacted both the reference solution within the electrode body and the unknown solution An appropriate metal probe (Ag, silver) coated with a layer of an insoluble salt (AgCl, silver chloride) of the metal immersed in the contained reference solution ("XMCl", molar concentration of metal chloride) served as the contact and provided a reference potential for the electrode. The selectivity of the electrode for a particular ion was determined by the composition of the glass membrane or the components included in the glass membrane. Such electrodes are referred to as "barrel" electrodes, and are described in detail in U.S. Pat. Nos. 3,598,713 and 3,502,560.

More recently, the development of synthetic, polymeric membranes as substitutes for the glass membrane has increased the list of ions that can be assayed potentiometrically by an ion selective electrode method. The synthetic membranes generally comprise a polymeric binder or support impregnated with an ion selective ionophore and a solvent for the ionophore. Membranes of this type are custom-designed to preferentially or selectively sense a predetermined ion by a judicious selection of the ionophore, ionophore solvent, polymeric binder and other adjuvants incorporated into the polymeric binder. These synthetic membranes and "barrel" electrodes containing these membranes as substitutes for the glass membranes are described in detail in U.S. Pat. Nos. 3,562,129, 3,691,047, and 3,753,887. Other patents relating to ion selective electrodes include Yamaguchi, et al. U.S. Pat. No. 4,839,020, disclosing a gas sensor to assay for carbon dioxide; Burgess et al. U.S. Pat. No. 4,818,361, disclosing a combination electrode to measure pH and free carbon dioxide; Watkins-Pitchford U.S. Pat. No. 4,743,352; and Conover et al. U.S. Pat. No. 4,713,165.

The principal advantage of the ion selective "barrel" electrodes, in addition to their high specificity, is that the electrode can be used repeatedly for measuring the concentration of the same ion in different solutions. Accordingly, the assay of a large number of samples for a specific predetermined ion can be performed by automated devices. Presently therefore, many types of ion selective electrodes are available to measure the ion content of a liquid. These ion selective electrodes have limitations, however, including the requirement for membranes comprised of specially designed polymer matrices; utilization of ionophores that require pre-neutralization with base to improve membrane sensitivity and to reduce response time; the need for storage under well-controlled conditions; short useful lifetimes; and loss of sensitivity and reliability during storage. In addition, some ion selective electrodes require relatively large samples (i.e., 1 ml, or greater) for accurate operation and are made of glass. Therefore, the ion selective electrode is costly, fragile and cannot be incorporated into a device suitable for automatically processing samples of very small size. Another major shortcoming of some ion selective electrodes is that after the first use of the electrode to determine the ionic activity of an unconditioned fluid, such as a body fluid, the exact composition of the electrode membrane, either glass or polymeric, is unknown due to contamination by previously-assayed test samples. Therefore, assay results often are suspect.

As stated previously, an ion selective electrode (ISE) can be designed to assay a test sample for a predetermined cation or a predetermined anion. For example, Chapoteau et al., in U.S. Pat. No. 4,810,351, disclosed an ion selective electrode that assays a test sample for carbonate ions. The ISE can be used in an automated assay device, such as the TECHNICON RA-1000® random-access discrete analyzer system, available from Technicon Instruments Corp., Tarrytown, N.Y., to assay 240 or more samples per hour. As will be demonstrated more fully hereinafter, the method of the present invention is especially useful in an ion selective electrode-based assay of a test sample for carbonate ion. However, the method of the present invention can be used in the detection and measurement of any anion or cation that can be assayed by ISE techniques. Accordingly, the following discussion relating to the assay of a test sample, like a biological fluid, for carbonate ion is merely illustrative. By using a heavy metal-free composition that buffers the test sample within the appropriate pH range for the assay of interest, the method of the present invention can be used to assay for any of a variety of anions or cations by an ion selective electrode including a membrane having the appropriate ionophore.

Therefore, the detection or measurement of carbonate ion, that in turn is related to the total carbon dioxide content of a biological sample, like blood serum or plasma, is a clinically important assay. This assay is used in the diagnosis and treatment of several potentially-serious disorders associated with changes in the acid-based balance in the body. The normal pH of plasma is 7.4 and defines the ratio of bicarbonate ion ($HCO_3^-$) to carbonic acid ($H_2CO_3$) in the test sample by the Henderson-Hasselbalch equation. Any disturbance in blood pH is compensated by appropriate responses of the respiratory and renal systems. Hence, more than one analysis is required to determine acid-based status. One such assay is the analysis of the total carbon dioxide content of the blood. Carbon dioxide dissolved in blood is in equilibrium between the interior of red blood cells and the plasma and also within the plasma. Carbon dioxide is present as dissolved carbon dioxide ($CO_2$), carbonic acid ($H_2CO_3$), bicarbonate ($HCO_3^-$), carbonate ($CO_3^{-2}$) and carbonate bound to free amino groups of proteins ($RNHCOO^-$). The total carbon dioxide concentration is defined as the sum of the concentrations of all forms of carbon dioxide that are present in the test sample.

In most assay methods for total carbon dioxide in blood serum or plasma, the biological fluid is added to an acidic reagent that converts bound carbon dioxide ($HCO_3^-$, $CO_3^{-2}$ and $RNHCO_2^-$) into free carbon dioxide ($H_2CO_3$ and dissolved $CO_2$). To determine total carbon dioxide, extraction methods, like dialysis, or equilibration methods measure the increase in pressure of gas at a fixed volume. In addition, potentiometric determination of the total carbon dioxide concentration has been performed using a carbonate-sensitive ion selective electrode. The ion selective electrode method requires fixing the pH of the test sample at a relatively high value, i.e., above about 8, by the addition of a buffered alkaline solution prior to testing, such as described in Herman and Rechnitz, *Anal. Chem. Acta.*, 76, pp. 155-164 (1975).

Carbonate-sensitive ion selective electrodes are described in Wise, U.S. Pat. No. 3,723,281; Kim et al., U.S. Pat. No. 4,272,328; Meyerhoff et al. *Anal. Chem. Acta*, 141, pp. 57-64 (1982) and Simon et al., *Anal. Chem.*, 54, pp. 423-429 (1982). A chloride-sensitive ion selective electrode is described in Oka et al , *Anal. Chem.*, 53, pp. 588-593 (1981). Each above-cited patent or publication attempted to provide a carbonate-sensitive ISE that was accurate, had an acceptable operating life, and exhibited minimal drift. The prior art references also attempted to eliminate or reduce the effects of interferents, like gentisate or salicylate, that often are present in the test sample.

The previously-described disclosed ion selective membrane electrodes useful for determination of total carbon dioxide in biological fluids in automated analyzers exhibit interference from several sources, like fatty acids, keto acids, salicylate and heparin. However, judicious selection of membrane components has provided a membrane with superior performance characteristics, like a short conditioning time, a long lifetime in storage, a rapid and stable response, low drift, and significantly less susceptibility to interference. Such electrodes can analyze 240 samples or more per hour, and assay results correlate well with assays performed by a dialysis method for total carbon dioxide.

Chapoteau et al., in U.S. Pat. No. 4,810,351, disclosed this type of carbonate-sensitive ISE that can be used in automated assays for carbonate ion. Chapoteau et al. disclosed a flow-through ion selective electrode, wherein a test sample is diluted at a 1 to about a 15 dilution ratio of test sample to buffer solution The buffer solution has a pH greater than about 8.2 such that the test sample includes carbonate ions. Furthermore, the buffer solution includes a heavy metal ion complex, like a mercury(II) ethylenediaminetetraacetate complex, to reduce the effects of interferents, like salicylate, that often are present in the test sample. The ISE disclosed by Chapoteau et al. is capable of assaying over two hundred samples per hour.

The ion selective electrode method of assaying for total carbon dioxide disclosed by Chapoteau et al. should be contrasted to the prior art methods. The determination of total carbon dioxide in automated flow systems customarily involved acidification of the sample, followed by dialysis of the resulting carbon dioxide gas into a recipient stream. The quantity of carbon dioxide dialyzed is proportional to the total carbon dioxide content of the sample. The resulting change in the pH of the recipient stream is measured either colorimetrically or with a pH electrode. However, neither method was practical at the very fast sampling rates of more than about 200 samples per hour in comparison to the use of an ion selective electrode that performs the required assay without dialysis Carbon dioxide reacts with water to form carbonic acid, that dissociates into bicarbonate ions and then into carbonate ions. The acid dissociation constants for these two dissociations is 6.37 and 10.25, respectively, at 25° C. In a buffered medium, then, a suitable ion selective sensor for carbon dioxide can be responsive to either carbonate or bicarbonate ion. A bicarbonate sensor has been used, but its response times are excessively long (5 to 15 min). Carbonate-responsive devices therefore are more commonly used, even though the sensitivity of the carbonate-sensitive ISE is only about one-half that expected for a bicarbonate sensor. Furthermore, a carbonate-sensitive ISE requires a relatively high pH for the sample, that usually is achieved by adding an alkaline buffer solution to the sample prior to the assay.

Initial attempts to produce an ion selective electrode for a carbonate determination were plagued by poor selectivity in the presence of chloride, by poor analytical slopes in the range of physiological concentrations, and by failure to control pH. In addition, relatively unstable liquid membranes having slow response times were used, and assay results were complicated by occasional unexplained high analytical recoveries. Furthermore, both endogenous and other common components of serum, like free fatty acids, heparin, coumadin and salicylate, can interfere with the response of carbonate sensors.

The continuously reusable carbonate-sensitive ISE disclosed in U.S. Pat. No. 4,810,351 also is described in the publication by W. J. Scott, E. Chapoteau and A. Kumar, "Ion-Selective Membrane Electrode for Rapid Automated Determinations of Total Carbon Dioxide", in *Clin. Chem.*, 3211, pp. 137-141 (1986). This electrode overcame many of the disadvantages of the prior art carbonate-sensitive and bicarbonate-sensitive ion selective electrodes. In addition, the ion-selective electrode could be arranged in sequence with sodium and potassium ion selective electrodes such that one test sample could be assayed for carbonate, sodium and potassium concentrations. The assays utilizing this carbonate-sensitive ISE are performed on a test sample diluted with a suitable buffer solution. The authors further stated that in addition to the components comprising the membrane of the ion selective electrode, the effects of anionic interferents present in the test sample also are further reduced by complexing the anionic interferents in solution, prior to the assay, with a suitable complexing reagent. Attempts to reduce the interfering effects of salicylate with ferric chloride, aluminum sulfate, caffeine, human serum albumin, or triazole were unsuccessful, as was an attempted carboxylation with peroxidase and an attempted oxidation with polyphenol oxidase or sodium hypochlorite. Another publication directed to an ion selective electrode assay method for carbonate ions is "Measurement of Total Carbon Dioxide Made at Low Range with an Ion Selective Electrode (TECHNICON RA-1000®)", W. J. Scott, E. Chapoteau and A. Kumar, *Clin. Chem.*, 32(11), p. 2119-2120 (1986).

Therefore, investigators generally attempted to reduce the effects of interferents by improving the design of the ion selective electrode membrane. The only known prior art method of effectively reducing the interfering effects of anionic compounds, such as salicylate, gentisate, hypaque, heparin and coumadin, in a test sample is to dilute the test sample with a buffer solution including a metal complex. The addition of a metal complex to reduce the effects of an anionic interferent in an ion selective electrode-based assay is disclosed by Kumar, in U.S. Pat. No. 4,196,056.

Kumar disclosed including a heavy metal complex in the diluting buffer solution to reduce the interfering effects of iodide ion and bromide ion in the assay for chloride ion with an ion selective electrode. The heavy metal complex forms soluble complexes with the bromide and iodide ions, and therefore the bromide and iodide ions are not available to interact with the ion selective electrode. It should be understood that this is important because the ion selective electrode used to assay for chloride ion also is responsive to bromide and iodide ions; and, if detected, the bromide and iodide ion concentrations would produce a measured chloride ion concentration far in excess of the actual chloride ion concentration because of the logarithmic measurement of the Nernst equation. The salicylate ion produces a similar response in the assay of a test sample for carbonate ion.

Although the method and composition disclosed by Kumar effectively reduce the effects of interfering anions, including iodide ions, bromide ions and other anions illustrated in the Scott et al. publication, the Kumar method and composition have the disadvantage of relying upon a heavy metal complex to reduce the effects of interferents. The metal complexes disclosed by Kumar include chelates of mercury, silver, lead, bismuth, copper and cadmium, and preferably include chelates of mercury(II). Many of these metals possess inherent toxicity, and therefore pose potential dangers to technicians that continually use buffers including the metal complexes Furthermore, considering the number of samples that are assayed (i.e. 240 or more per hour) and the dilution ratio of test sample to buffer (1 to at least 10), a relatively large volume of waste material is generated. According to the method of Kumar, this waste material includes a heavy metal, and therefore is difficult to dispose of safely and economically.

However, in accordance with an important feature of the present invention, a heavy metal-free composition is used to dilute and buffer the test sample. Surprisingly, the heavy metal-free composition effectively reduces the effects of interferents present in the test sample, while maintaining electrode sensitivity and maintaining a useful electrode lifetime. The composition and method of the present invention include a buffering compound, and preferably a borate compound, to dilute the test sample, to buffer the test sample at a suitable pH, and to reduce the effects of interferents. In addition to the buffering compound, the composition includes an alkalinity adjusting compound to provide a suitable pH for the particular assay of interest. For example, in the assay for carbonate ion, tetramethylammonium hydroxide and a borate compound provide a buffering composition having suitably high pH such that all of the carbon dioxide species in the test sample are converted to the carbonate ion. In the case of an assay for carbonate ion, the buffering composition also includes a small amount of bicarbonate ions to provide a small background amount of carbonate ions Optionally, the buffering composition includes a nonionic surface active agent to help improve ISE responses by enhancing the wash characteristics of the flowing stream. It should be understood that the metal-free composition includes a buffering compound, like a borate, to buffer the diluted test sample and to eliminate the effects of interferents.

If the ion selective electrode-based assay is for an analyte other than carbonate, then an alkalinity adjusting compound is selected to provide the appropriate pH for that particular analyte. In addition, the optional bicarbonate anion is eliminated, and, if desired, replaced by another suitable compound to provide a background concentration of the analyte of interest. Furthermore, for any analyte that is assayed between a pH of about 5 and about 11, a borate compound can serve as a buffer and to reduce the effects of an interferent. Outside of the pH range of from about 5 to about 11, the borate compound still is added to reduce the effects of an interferent, but a separate buffering compound should be added to maintain the diluted test sample at the desired pH.

Prior art electrodes have utilized a borate compound as a buffering agent. For example, Macur, in U.S. Pat. No. 3,957,613, disclosed a miniature probe for simultaneously sensing ions and gaseous partial pressures. The partial pressure sensor for gases includes a gas-permeable membrane enclosing a compartment filled with a borate buffer at pH 4.8 to 5.4. Butler, in U.S. Pat. No. 4,060,750, disclosed a thin film polarographic sensor that can utilize a borate buffer. Neither device is similar to the ion selective electrodes and method utilized in the present invention.

Accordingly, it has been found that the heavy metal-free composition of the present invention provides accurate and sensitive assays for a predetermined analyte in an ion selective electrode assay technique. The heavy metal-free composition can be used in automated assay devices wherein a single predetermined analyte in the test sample is assayed, or wherein several predetermined analytes are assayed in sequence by different ion selective electrodes. In addition, the heavy metal-free composition is safer to use, and waste disposal problems of the spent composition are overcome. Hence, in contrast to the prior art, new and unexpected results are achieved in the ion selective electrode-based assay of a predetermined analyte in a test sample, like blood plasma or serum, by utilizing a heavy metal-free composition as the buffering composition to dilute and buffer the test sample and to substantially reduce the effects of interferents often present in the test sample The heavy metal-free composition also maintains the selectivity of the ion selective electrode, and maintains the operating lifetime of the ion selective electrode. The heavy metal-free composition is especially useful in an ion selective electrode assay method for carbonate ion concentration in a test sample.

SUMMARY OF THE INVENTION

In brief, the present invention is directed to a heavy metal-free composition used to dilute and buffer a test sample in an ion selective electrode method of assaying for a predetermined analyte. Surprisingly, the heavy metal-free composition has been found to substantially reduce the effects of interferents on the ion selective electrode-based assay. Previously, such a reduction in affects of interferents was observed only if a heavy metal complex was included in the buffering composition. Therefore, the heavy metal-free composition of the present invention includes a borate compound that unexpectedly, substantially reduces the effects of interferents that often are present in a test sample. The heavy metal-free composition also includes an alkalinity adjusting compound, either acidic or alkaline, to provide a suitable pH to accurately assay the test sample for the predetermined analyte of interest.

The heavy metal-free composition is used in an ion selective electrode assay method for the presence or concentration of a predetermined analyte, like carbonate ion, in a test sample, such as a biological fluid, like blood plasma or serum. The heavy metal-free composition dilutes the test sample, buffers the test sample and, surprisingly, effectively reduces the effects of interferents present in test sample on the ion selective electrode assay. Accordingly, the heavy metal-free composition provides a more sensitive and an accurate ion selective electrode analyte assay, and avoids the use of potentially-toxic heavy metal complexes that were included in prior art buffering compositions. In addition, the heavy metal-free composition does not adversely affect the useful life of the ion selective electrode, does not adversely affect the counter-flow reference electrode, and does not generate a potentially-toxic waste product.

Therefore, in accordance with an important feature of the present invention, an improved buffering composition for use in an ion selective electrode-based assay for the presence or concentration of a predetermined analyte is provided. The aqueous buffering composition is essentially free of heavy metal ions and includes: a) a borate compound to buffer the test sample at a suitable pH for the assay of interest and to reduce the effects of interferents present in the test sample; and b) an alkalinity adjusting compound, either alkaline or acidic, to provide a suitable pH for the ion selective electrode-based assay of the predetermined analyte of interest It should be understood that a borate compound is used as the buffering compound in the pH range of from about 5 to about 11. Therefore, if the suitable pH for the ion selective electrode-based assay of the predetermined analyte of interest is outside the pH range of from about 5 to about 11, an additional buffering compound can be included in the composition to buffer the test sample at the appropriate pH. However, the borate compound nevertheless is included in the heavy metal-free composition to substantially reduce the effects of interferents present in the test sample. Furthermore, the heavy metal-free buffering composition optionally can include a sufficient amount of the predetermined analyte to provide a low background response and improve the linear response of the ion selective electrode; and any other ingredients, like a nonionic surfactant, that do not adversely affect the response of the ion selective electrode to the predetermined analyte. However, the buffering composition of the present invention is essentially free of any heavy metal complexes, such as mercury complexes.

The heavy metal-free composition is used in ion selective electrode-based assays of a test sample, and especially of a biological sample, such as blood plasma, blood serum, cerebrospinal fluid or urine. The heavy metal-free composition is especially useful in the assay of blood plasma or serum for total carbon dioxide by measuring the amount of carbonate ion in the plasma or serum via an ion selective electrode. The heavy metal-free composition can be used in automated ion selective electrode assay devices, and can be used in automated assay devices that assay a single test sample for more than one analyte by positioning different ion selective electrodes in sequence.

In particular, the essentially heavy metal-free composition includes: a) from about 0.3% to about 5%, and preferably from about 1% to about 4%, by weight of a borate compound, such as boric acid; and b) a sufficient amount of an alkalinity adjusting compound, either alkaline or acidic, like tetramethylammonium hydroxide, to provide a suitable pH for the assay of interest. The composition optionally can include a sufficient amount of the predetermined analyte to provide a background response for the ion selective electrode; a nonionic surfactant, like an ethoxylated octylphenol, in an amount from 0% to about 0.5% by weight of the composition, to help speed the homogeneous dilution of the test sample by the heavy metal-free composition and to improve ion selective electrode response to the predetermined analyte; or an additional buffering compound, especially if the assay for the predetermined analyte is conducted outside the pH range wherein the borate compound can serve as a buffering compound. As an added advantage, the heavy metal-free composition does not require a preservative because the borate compound also acts as a preservative. The ability to eliminate a preservative from the buffering composition is important because often the preservative and the ISE membrane are incompatible.

The heavy metal-free composition is used to dilute and buffer the test sample by adding the heavy metal-free composition to the test sample in a ratio of from about 3 parts to about 25 parts of heavy metal-free composition to 1 part of test sample. Preferably, the ratio of heavy metal-free composition to test sample is in the range of from about 5 parts to about 20 parts to 1 part. Dilution of the test sample with the heavy metal-free composition provides a solution of fixed pH and constant ionic strength The resulting buffered mixture of the test sample and the heavy metal-free composition is analyzed for the amount of predetermined analyte in the test sample by an ion selective electrode. The response of the ion selective electrode then is correlated to the amount of predetermined analyte in the test sample. In an automated analyzer, the mixture subsequently can be assayed by other ion selective electrodes for the presence or concentration of other predetermined analytes in the test sample. After all the ion selective electrode assays are completed, the mixture is discarded. In accordance, with an important feature of the present invention, the spent mixture can be safely, easily and economically discarded because potentially-toxic heavy metals are not present in the spent mixture of sample and buffering composition.

It was found that the heavy metal-free composition provided sensitive assays for the predetermined analyte; substantially reduced the effects of interferents on the ion selective electrode-based assay; did not adversely affect the membrane of the ion selective electrode that includes the ionophore and separates the reference liquid from the diluted test sample; is easy and safe to prepare, use and discard; and maintains the selectivity and lifetime of the electrode.

BRIEF DESCRIPTION OF THE DRAWINGS

The above and other aspects and advantages and novel features of the present invention will become apparent from the following detailed description of the invention, as illustrated in the accompanying figures, describing the heavy metal-free composition of the present invention and its use in an ion selective electrode-based assay of a test sample for a predetermined analyte.

DETAILED DESCRIPTION OF THE INVENTION

Figure 1:
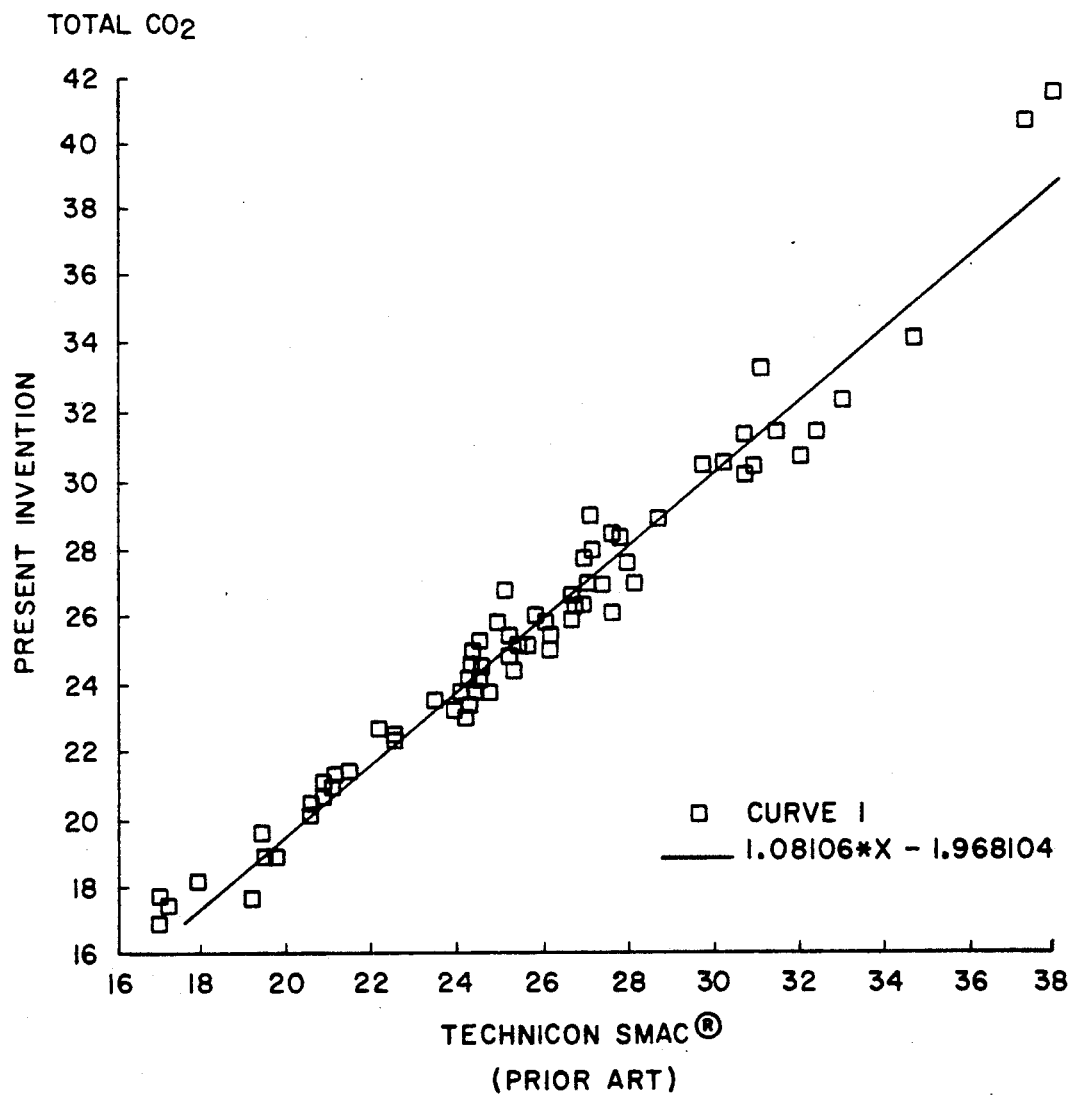
FIG. 1 is a plot showing the correlation of results of assays for total carbon dioxide, i.e. carbonate ion, performed on test samples including from about 16 mM (millimolar) to about 42 mM of total carbon dioxide; the y-axis plots assay results obtained from ion selective electrode-based assays using a metal-free composition of the present invention and the x-axis plots assay results of the same test sample obtained by a prior art method.

The ion selective electrode-based assay of a test sample for a predetermined analyte is well-known and is discussed thoroughly in the prior art. However, interfering compounds often present in the test sample have been a long-standing problem and have limited the use of ion selective electrodes in assays because the assay result was unreliable. In general, the presence of interfering compounds results in an apparent concentration of the predetermined analyte that is substantially greater than the actual concentration of the predetermined analyte.

Investigators realized that if the effects attributed to these interfering compounds were reduced or eliminated, then the accuracy and reliability of an ion selective electrode-based assay would increase significantly. Furthermore, the development of a reliable and accurate ion selective electrode assay method would be advantageous because ion selective electrode-based assays are ideally-suited for use in automated analyzers that are capable of performing hundreds of assays per hour.

Ion selective electrodes are especially useful in automated analyzers because these electrodes are reusable, are sensitive, perform assays quickly, and can be positioned in sequence to assay a single test sample for a variety of analytes Accordingly, when it was found that the effects of interferents present in a test sample were substantially reduced by including a heavy metal complex in the buffer solution used to dilute the test sample, the accuracy of an ion selective electrode assay was increased Consequently, the use of an ion selective electrode to assay for a predetermined analyte increased. However, the use of a heavy metal-containing buffer solution created problems in disposing of the relatively large volumes of spent, diluted sample contaminated with a heavy metal, usually mercury. The potential toxicity of the heavy metal-containing buffer also presented health concerns to technicians that continually handle the buffer solution and the spent diluted samples.

Therefore, in accordance with an important feature of the present invention, an essentially heavy metal-free buffer composition has been found that dilutes the test sample; buffers the test sample; substantially reduces the effects of interferents present in the test sample; does not adversely affect the membrane of the ion selective electrode; maintains electrode sensitivity; maintains the useful life of the electrode; and improves the sensitivity of the ion selective electrode-based assay. The heavy metal-free composition is especially useful in the ion selective electrode-base assay for carbonate ion in a test sample. In particular, the heavy metal-free composition is useful in the ion selective electrode-based assay of a biological fluid, like blood plasma, blood serum, cerebrospinal fluid or urine, for total carbon dioxide content by assaying the biological fluid for carbonate ion. However, the heavy metal-free composition also can be used in ISE-based assays of other fluids, like urine, for other analytes of interest, such as chloride ion, sodium ion and potassium ion. Accordingly, the heavy metal-free buffer composition is ideally-suited for use in automated analyzers, and especially in automated analyzers having different ion selective electrodes positioned in sequence to analyze a single test sample for a variety of analytes.

The heavy metal-free buffer composition of the present invention reduces the effects of interferents present in the test sample as effectively as the mercury-containing buffer compositions disclosed and practiced in the prior art. Furthermore, the buffer compositions of the present invention demonstrate an increased sensitivity to the predetermined analyte of interest; are more safely handled; and are more safely and more economically disposed. It should be understood that the term "metal-free" in metal-free composition refers to heavy metals, such as mercury, lead, cadmium, silver, bismuth and copper, used in the prior art to reduce the effects of interferents present in the test sample. The term, however, does not refer to alkali metals that can be included in the metal-free composition of the present invention, for example, either as a component of the alkalinity adjusting compound, as a component of the compound providing a background response of predetermined analyte, or as a component of any other essential or optionally-included compound. Metals that can be present in the heavy metal-free composition include, for example, sodium, potassium, and lithium.

The interferents that often are present in the test sample in addition to the predetermined analyte of interest include, for example, bromide ion, iodide ion, salicylate, coumadin, gentisate, heparin, hypaque, ibuprofen, nitrate and cyanide. Unless such interferents are separated from the test sample, or otherwise rendered incapable of interacting with the ionophore present in the membrane of the ion selective electrode, an erroneously high assay for the predetermined analyte of interest will result. Although the prior art compositions of Kumar, disclosed in U.S. Pat. No. 4,196,056, reduced the effects of such interferents, the disclosed compositions included toxic heavy metals, thereby making handling of the composition potentially hazardous and disposal of the spent composition difficult and expensive. However, the improved, heavy metal-free composition of the present invention not only substantially reduces the effects of interferents, but also provides a more sensitive assay and allows for the safe, easy and economical handling and disposal of the metal-free composition.

For purposes of illustration, the following detailed description of the invention provides an embodiment of a heavy metal-free composition that can be used in the ion selective electrode-based assay for carbonate ion. However, it should be understood that with the appropriate choice of an alkalinity adjusting compound and optional ingredients, the borate-containing buffer composition of the present invention can be used in the ion selective electrode-based assay of many other predetermined analytes as well.

Therefore, the metal-free composition of the present invention is an aqueous composition comprising: (a) from about 0.3% to about 5%, and preferably from about 1% to about 4%, by weight of the composition of a borate compound, such as boric acid; and (b) a sufficient amount of an alkalinity adjusting compound to provide a suitable pH for the assay of interest. If the pH of the assay is within the limits wherein the borate acts as a buffer, an additional buffer can be added to the composition if desired. However, within this pH range, of from about 5 to about 11, the borate compound can serve as the buffer. Outside of the pH range wherein the borate compound acts as a buffer, a suitable buffer for that particular pH range should be added to the metal-free composition. Optionally, the metal-free composition can include a small, but sufficient, amount of the predetermined analyte to provide a background response; and can include from 0% to about 0.5% of a nonionic surfactant to improve the linearity of the electrode response. Other optional ingredients that do not materially interfere with the ion selective electrode-based assay for the predetermined analyte of interest also can be included in the heavy metal-free composition.

In accordance with an important feature of the present invention, the heavy metal-free composition includes a borate compound in an amount ranging from about 0.3% to about 5% by weight of the composition. Preferably, the composition includes from about 1% to about 4% of the borate compound by weight; to achieve the full advantage of the present invention, the heavy metal-free composition includes from about 1.5% to about 3% of the borate compound by weight of the composition. It has been found that the borate compound substantially reduces the effects of interferents that are present in the test sample. In addition, if the ion selective electrode-based assay is performed in the pH range of from about 5 to about 11, the borate compound also acts as a buffering agent. As will be demonstrated more fully hereinafter, the borate compound reduces the effects of interferents at least as well as the mercury complexes disclosed in the prior art, and also avoids the toxicity problems associated with handling and disposing of heavy metal ions, like mercury.

To achieve the full advantage of the present invention, boric acid or sodium tetraborate is included as the borate compound in the heavy metal-free composition. However, other borates, such as sodium metaborate, also are envisioned as being useful in the method of the present invention. Boric acid and sodium tetraborate are preferred because these compounds are easily adjusted by an acid or a base to provide a pH suitable for the ion selective electrode-based assay of a predetermined analyte. In general however, any borate compound capable of complexing with an interferent present in the test sample can be utilized in the method and composition of the present invention.

For example, boric acid is known to complex with salicylic acid to provide the borosalicylate complex (I). (A. Martell and M. Calvin, "Chemistry of the Metal Chelate Compounds", Prentice-Hall, Inc., p. 48 (1952)). Accordingly, if salicylate is present in the test sample, it will complex with the

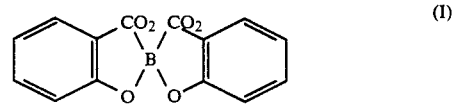

(I)

boric acid or other borate compound, and therefore be unavailable to interact with the ionophore present in the membrane of the ion selective electrode. Other literature references relating to boric acid reactions with salicylate ion include:

1. A. Queen, et al., "The Kinetics of the Reactions of Boric Acid with 5-Substituted Salicylate Ions", *Can. J. Chem.*, 57(8), pp. 920-923 (1979), (salicylate ion forms 1:1 complex with boric acid);

2. O. Lukkari and J. Tamminen, "Equilibria of Nitrosalicylic Acids: Complex Formation Between Boric Acid and Salicylic and Nitrosalicylic Acids", *Finn. Chem. Lett.*, 15(1-2), pp. 13-17 (1988), (1:1 complexes formed and were studied at pH 5.2);

3. V. Grundsteins, et al., "Reaction In the Boric Acid—Salicylic Acid System", *Latv. PSR Zinat. Akad. Vestis, Kim.-Ser.*, 2, pp. 131-135 (1978);

4. E. Bottari, et al., "On the Reaction Between Boric Acid and Salicylate Ions", *Ann. Chim. (Rome)*, 68(9-10), pp. 791-800 (1978), (complexes not confirmed in concentration range studied); and 5. T. L. Paal, "Study of the Weak Interactions Operating Between Boric Acid and Polar Organic Compounds in Aqueous Solutions", *Acta Chim. Acad. Sci. Hung.*, 103(2), pp. 193-198 (1980), (polar compounds studied include dioxane, acetone, cyanomethane, propane and butanol; and the formation of boric acid complex with Lewis bases is discussed).

Similarly, the gentisate anion, another known interferent, has the structural formula (II). The gentisate anion is structurally related to the salicylate anion with a hydroxyl group and a carboxyl group on adjacent carbon atoms of the benzene ring. Therefore, the gentisate

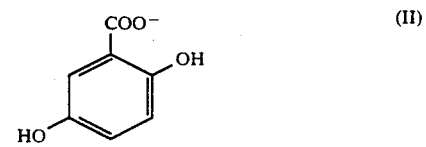

(II)

anion also complexes with the borate compound, and consequently be essentially unavailable to interact with the ionophore in the membrane of the ion selective electrode. Similarly, sodium heparin has a carboxyl group and a hydroxyl group in sufficient proximity to complex with the borate compound Therefore, any borate compound that is sufficiently soluble in water, i.e. having a water solubility of at least about 0.3 g (gram) per 100 g of water, and that can interact with the interferents usually found in a test sample, and especially anionic interferents found in a biological fluid, is useful in the heavy metal-free composition of the present invention.

The heavy metal-free composition of the present invention also includes an alkalinity adjusting compound to provide a suitable pH to assay for the predetermined analyte of interest. For example, in an assay method for total carbon dioxide present in a blood serum sample using an ion selective electrode, all the forms of carbon dioxide present in the test sample are converted to carbonate ion, and a carbonate-sensitive ion selective electrode is used to assay the blood serum sample. As previously discussed, blood has a pH of about 7.4 and the carbon dioxide is present as free carbon dioxide, carbonic acid, bicarbonate, carbonate, and carbonate bound to proteins. Therefore, to assay for total carbon dioxide by measuring carbonate ion concentration, the pH of the blood serum sample is increased to a pH of greater than about 8.2 to convert a portion of the various fixed and free forms of carbon dioxide to carbonate ion. The pH of the blood serum sample is increased by diluting the blood serum with a heavy metal-free composition of the present invention that has a suitably high pH, such as above about 8.2.

Consequently, in the ion selective electrode-based assay for carbonate ion, the metal-free composition includes, for example, tetramethylammonium hydroxide, as the alkalinity adjusting compound. In the ion selective electrode-based assay for carbonate ion, a sufficient amount of alkalinity adjusting compound is included in the metal-free composition such that the test sample pH is increased to greater than about 8.2, and usually to about 8.3 to about 8.5. Accordingly, tetramethylammonium hydroxide is included in the heavy metal-free composition in a sufficient amount, such as from about 0.1% to about 2% by weight of the composition, to increase the pH of the borate-containing composition above about 8.2. However, it should be understood that the amount of alkalinity adjusting compound included in the composition varies depending upon the identity of the alkalinity adjusting compound, the pH of the test sample and the suitable pH for conducting the assay. In some instances, an alkaline alkalinity adjusting compound is included in the metal-free composition to increase the pH of the test sample, as exemplified in the ion selective electrode-based carbonate assay of blood serum or plasma. Other suitable alkaline alkalinity adjusting compounds include, but are not limited to, potassium hydroxide, ammonium hydroxide, sodium hydroxide, lithium hydroxide, barium hydroxide, magnesium hydroxide, calcium hydroxide, tetrabutylammonium hydroxide, tetraethylammonium hydroxide and similar mono-, di-, tri-, and tetra-substituted alkylammonium hydroxides, wherein the alkyl group includes from one to about four carbon atoms, or combinations thereof. However, in the assay for a different predetermined analyte, an acidic alkalinity adjusting compound can be added to the heavy metal-free composition to lower the pH of the test sample. For example, the ion selective electrode-based assay for chloride ion concentration is performed at a pH of about 6. Suitable acidic alkalinity adjusting compounds include, but are not limited to, hydrochloric acid, phosphoric acid, hydrofluoric acid, sulfuric acid, acetic acid, and nitric acid, or combinations thereof.

The actual identity of the alkalinity adjusting compound is not particularly limited, provided that the alkalinity adjusting compound is water soluble and adjusts the pH of the heavy metal-free composition to a suitable pH value such that when one part of the test sample is diluted with from about 3 parts to about 25 parts of the heavy metal-free composition, the pH of the resulting mixture is the desired pH for the assay of the predetermined analyte of interest. In addition, the alkalinity adjusting compound should be selected such that the alkalinity adjusting compound does not interfere with the assay for the predetermined ion of interest. For example, sodium carbonate should not be used to increase the pH of a borate-containing composition of the present invention to a value above 8.2 in an assay for carbonate ions, or for sodium ions, because the alkalinity adjusting compound then could interfere with the ion selective electrode-based assay. Similarly, hydrochloric acid should not be used as the alkalinity adjusting compound to decrease the pH of the heavy metal-free buffering composition in an ion selective electrode-based assay for chloride ion. In either case, the use of a carbonate or of a chloride alkalinity adjusting compound could interfere in the assay for that particular analyte.

Accordingly, the metal-free composition of the present invention includes a borate compound and an alkalinity adjusting compound. These ingredients reduce the effects of interferents on the ion selective electrode-based assay and provide the desired pH for the assay. However, the metal-free composition also should exhibit a sufficient buffering capacity. If the pH of the heavy metal-free composition is within the range of about 5 to about 11, an additional buffering agent can be, but does not have to be, included in the metal-free composition. Within this pH range, the borate compound acts as the buffering agent. In general, a borate buffer is preferred in the pH range of about 5 to about 11 because borate buffers can be usefully employed to assay for a range of analytes at a greater ionic strength than a buffer such as TRIS hydrochloride (TRIS·HCl).

However, outside the pH range of from about 5 to about 11, the borate compound is not an effective buffer, and an additional buffering agent can be included in the metal-free composition. It should be understood that an additional buffering agent also can be included in the metal-free composition in the pH range of from about 5 to about 11, if desired, as long as the selected buffering agent does not adversely affect the ion selective electrode-based assay.

For example, the buffering agent can be selected from the Good's buffers exemplified in TABLE I. Such buffers, or a combination of buffers, impart a buffering capacity to the metal-free composition within

TABLE I

| Good's Buffer | Useful pH Range |
|---|---|
| MES* | 5.5–6.7 |
| BIS-TRIS | 5.8–7.2 |
| ADA | 6.0–7.2 |

TABLE I-continued

| Good's Buffer | Useful pH Range |
|---|---|
| PIPES | 6.1–7.5 |
| ACES | 6.1–7.5 |
| BIS-TRIS PROPANE | 6.3–9.5 |
| MOPSO | 6.2–7.6 |
| BES | 6.4–7.8 |
| MOPS | 6.5–7.9 |
| TES | 6.8–8.2 |
| HEPES | 6.8–8.2 |
| TAPSO | 7.0–8.2 |
| HEPPSO | 7.1–8.5 |
| DIPSO | 7.0–8.2 |
| POPSO | 7.2–8.5 |
| EPPS | 7.3–8.7 |
| TRIS | 7.0–9.0 |
| TRICINE | 7.4–8.8 |
| BICINE | 7.6–9.0 |
| TAPS | 7.7–9.1 |
| AMPSO | 8.3–9.7 |
| CHES | 8.6–10.0 |
| CAPSO | 8.9–10.3 |
| CAPS | 9.7–11.1 |

*Abbreviations for Good's Buffers, the full chemical name for each buffer is found in the 1987 catalog of Sigma Chemical Co., St. Louis, MO., pages 306–309.

the pH range of from about 5.5 to about 11.1. Other buffering agents include, but are not limited to, glycine, glycylglycine, ethanolamine, imidazole, triethanolamine, acetate, 2-amino-2-methyl-1-propanol, 2-amino-2-methyl-1,3-propanediol, 3-amino-1-propanesulfonic acid, citrate, lactate, phosphate, phthalate, trichloroacetate, sulfosalicylate, maleic acid, 3,3-dimethylglutaric acid, succinate and combinations thereof. It also should be understood that the selection of the buffering agent is influenced by the identity of the predetermined ion of interest. For example, a buffering agent that interferes with the ion selective electrode-based assay of the analyte of interest should be avoided. Such a determination is easily made by a person having ordinary skill in the art of ion selective electrode-based assays. For example, a TRIS buffer can interfere in the ion selective electrode-based assay for potassium ion.

Although the compounds listed in TABLE I are suitable buffers, it has been found that the heavy metal-free composition of the present invention nevertheless requires a borate compound to reduce the effects of an interfering compound that is present in the test sample and to provide a more sensitive assay for the predetermined ion of interest. To demonstrate that a borate compound is an essential ingredient of the present invention, metal-free compositions, buffered in a suitable pH range to assay for carbonate ion, but absent a borate compound, were used in an ion selective electrode-based assay for carbonate ion. For example, the buffers, TRIS (at 0.3M, 0.1M, and 0.05M), glycylglycine (at 0.1M and 0.3M), BICINE (at 0.3M), TRICINE (at 0.3M), HEPPS (at 0.3M) and TAPS (AT 0.3M), were used in an ion-selective electrode-based assay for carbonate.

In general, the buffers, in the absence of borate, demonstrated a smaller Nernstian slope, and therefore provided a less sensitive assay; and demonstrated a decreased ability to reduce the effects of salicylate ion on the assay for carbonate ion. As will be discussed in more detail hereinafter, assays utilizing only a buffer listed in TABLE I did not satisfactorily equilibrate with the ion selective electrode, and therefore were automatically flagged by the automated assay device. In general, flagging indicates a relatively high degree of interference. In contrast, a borate-containing buffer of the present invention significantly reduced the number of flagged assays in assays of test samples including salicylate ion.

Specifically, assays utilizing a metal-free composition of the present invention provided a Nernstian slope of from about 22.5 to about 24.2 over a seven day period in an automated carbonate assay, and the observed salicylate effect was less than about 2 mM/L for the first two days. However, the buffers listed in TABLE I could not be used for seven days; demonstrated a salicylate effect far above 2 mM/L on the second day; and, except for TRIS, exhibited significantly smaller Nernstian slopes than the metal-free composition of the present invention. In addition, a borate-containing, metal-free composition of the present invention is stable upon storage under normal conditions, whereas some of the other tested buffers, such as glycylglycine and BICINE, were not stable for more than one to two days. For example, large crystals were observed in the BICINE buffer within two days.

The two essential ingredients, i.e. the borate compound and the alkalinity adjusting compound, and any additional buffering agents, are dissolved in water to provide an aqueous metal-free composition of the present invention. Preferably, the aqueous metal-free composition does not include organic solvents that may adversely affect the membrane of the ion selective electrode, such as by extracting the hydrophobic components, like the ionophore, included in the membrane. However, an organic solvent, such as an alcohol, can be included in the metal-free composition to help solubilize an ingredient of the metal-free composition, as long as the organic solvent is present in an amount of about 2% or less by weight of the composition.

The metal-free composition of the present invention also can include optional ingredients to improve the response of the ion selective electrode or to otherwise improve the reliability, sensitivity and accuracy of the ion selective electrode-based assay. For example, the metal-free composition can include a low concentration of the predetermined ion of interest to provide a background response from the ion selective electrode This background response extends the linear range of the response of the ion selective electrode to encompass the concentration range of the predetermined analyte in the test sample. The amount of predetermined analyte included in the metal-free composition to provide a background response is varied, and is dependent upon the particular predetermined analyte of interest and particular experimental parameters, such as the dilution ratio.

For example, in the ion selective electrode assay method for carbonate ion, the metal-free composition can include a low concentration of carbonate ion. This concentration of carbonate ion is provided by including a bicarbonate compound in the metal-free composition in an amount ranging from 0% to about 0.03%, and preferably from 0% to about 0.01%, by weight of the composition. Suitable compounds to provide a background response of predetermined analyte (i.e. carbonate) include, but are not limited to, sodium bicarbonate, potassium bicarbonate, ammonium bicarbonate, lithium bicarbonate, and combinations thereof.

If the predetermined analyte is an ion other than carbonate, a small background concentration of that particular ion of interest can be added. For example, a small background amount, such as about 1 mM/L of potassium ion, sodium ion or chloride ion can be added to a metal-free composition used in an assay for that particular ion. Furthermore, if the metal-free composition is used to dilute a test sample that will be analyzed for more than one predetermined analyte, a background concentration for each predetermined ion can be included in the metal-free composition. In every case, however, the amount of predetermined ion included in the metal-free composition is sufficiently low to provide a background response that does not swamp or mask clinically-significant amounts of the predetermined ion in the test sample.

The metal-free composition also can include, optionally, a nonionic surfactant to facilitate the rapid and homogeneous mixing of the test sample throughout the metal-free composition and to improve the response of the ion selective electrode. Often the test sample is a comparatively thick or viscous liquid. Therefore, a surface active agent helps wetting and dispersal of the test sample for rapid and complete solubilization of the test sample in the heavy metal-free composition. Furthermore, the nonionic surfactant decreases the surface tension of the metal-free composition, thereby allowing a more intimate contact between the hydrophobic membrane of the ion selective electrode and the test sample components diluted in the metal-free composition. It also is known that certain ionic species can interfere in ion selective electrode-based assays. Therefore, if an optional surfactant is included in the metal-free composition, anionic and cationic surfactants generally should be avoided.

It also should be understood that although a nonionic surfactant generally does not interfere in the ion selective electrode assay, if the concentration of the optional nonionic surfactant in the metal-free composition is too great, the nonionic surfactant can adversely affect the membrane of the ion selective electrode. For example, the nonionic surfactant can extract or solubilize the hydrophobic ionophore or the hydrophobic plasticizer from the membrane, and therefore lead to a premature failure of the ion selective electrode. This phenomenon is especially important in automated assay systems wherein the ion selective electrode essentially is in constant contact with the test sample diluted in the metal-free composition.

Therefore, the metal-free composition optionally can include from 0% to about 0.5% of a nonionic surfactant by weight of the metal-free composition. Suitable nonionic surfactants are water-soluble and include, for example, ethoxylated or propoxylated nonlyphenols or octylphenols, ethoxylated or propoxylated fatty alcohols, ethylene oxide-propylene oxide copolymers, polyethylene oxides, ethoxylated fatty esters, glycerol esters, phosphate esters, silicon-based surfactants and other well-known water-soluble nonionic surfactants as listed in *McCutcheon's Emulsifiers and Detergents,* McCutcheon Div., MC Publishing, Glen Rock, N.J. (1989). In addition to the above-described optional ingredients, other optional ingredients, like colorizing agents or ionic strength adjusting agents, also can be included in the metal-free composition as long as the optional ingredients do not adversely affect the sensitivity or accuracy of the ion selective electrode-based assay.

To demonstrate the new and unexpected results provided by the metal-free composition and the method of the present invention, the following metal-free composition was prepared and used in an ion selective electrode-based assay for carbonate ion. The metal-free composition of Example 1 was prepared by simply adding the ingredients, in the listed order and with stirring, to provide a metal-free composition having a pH buffered in the range of 8.35 to 8.45.

EXAMPLE 1

| Metal-Free Composition | |
|---|---|
| Ingredient | % (by weight) |
| Water, deionized | 97.61 |
| Nonionic Surfactant[1] | 0.05 |
| Tetramethylammonium Hydroxide[2] | 0.56 |
| Boric Acid | 1.77 |
| Sodium Bicarbonate | 0.01 |
| Total | 100.00 |

[1] Ethoxylated octylphenol, TRITON X-100, Rohm and Haas, Philadelphia, PA.
[2] Added as 61.5 ml of a 1M solution.

The metal-free composition of Example 1 then was used in a series of ion selective electrode-based assays of test samples for carbonate ion. The ion selective electrode utilized in the carbonate assays is that described by Chapoteau et al. in U.S. Pat. No. 4,810,351, herein incorporated by reference.

For the automated ion selective electrode-based assay of carbonate ion, a TECHNICON RA-1000 ® "random-access" discrete analyzer system, available from Technicon Instruments Corp., Tarrytown, N.Y., and equipped with a module including the ion selective electrodes, was used. A 25 μL (microliter) test sample was aspirated into a reaction tray; diluted 14-fold with the metal-free composition of Example 1; mixed in a reaction chamber; then the diluted sample was aspirated into the electrode module that holds ion selective electrodes for potassium, sodium, and carbonate ions. The electrode module also received a counter-flow solution that flows past a silver/silver chloride reference electrode. The automated analyzer measured the difference in potential between the reference and sample electrodes in response to the concentrations of potassium, sodium, and carbonate ions in the test sample, and printed the calculated ion concentrations from appropriate calibration data stored in memory. The carbonate-sensitive ion selective electrode is continuously reusable, and the reagents, dilution factors, and other parameters were chosen such that sodium ion and potassium ion concentrations also could be measured by ion selective electrodes on line with the carbonate sensor. Accordingly, three measurements can be made on each of at least 240 samples, for at least 720 assays per hour.

In the ion selective electrode-based assay, the membrane of the ion selective electrode is mounted on a flowthrough electrode assembly, either a TECHNICON RA-1000 ® electrode block assembly that can include more than one ion selective electrode or a single electrode mount assembly. A single flowthrough unit is attached to a counter-flow reference block, then the outputs from the reference and sensing electrodes are fed to an amplifier. The reference electrode is in contact with counter-flow potassium chloride reference solution, while the ion-selective membrane contacts the sample diluted with an alkaline pH buffer, i.e. a metal-free composition of the present invention that includes a borate compound to decrease potential anionic interferences. The produced carbonate ions are sensed by the ion selective electrode. This electrode system was standardized with two aqueous sodium bicarbonate calibrators that also contained sodium and potassium chloride.

Assay results for test samples including an unknown concentration of carbonate ion were calculated either automatically or manually by using the standard Nernst relationships.

As an added advantage of the present invention, if the metal-free buffer composition accidentally contacts the counter-flow silver chloride reference electrode, the reference electrode is not destabilized. Instability of the reference electrode has been demonstrated when a metal-containing prior art buffer solution contacts the reference electrode because TRIS-based buffer can dissolve, or deplate, the silver chloride from the reference electrode. A borate buffer does not deplate the reference electrode.

As will be demonstrated more fully hereinafter, the metal-free composition of the present invention was used to dilute and buffer test samples, and to substantially reduce the interfering effects of compounds often present in the test samples. The prior art described several attempts to reduce the effects of interferents by optimizing the design of the ion selective electrode. However, the present invention is directed to improving the response of an ion selective electrode by the use of a metal-free buffering composition. Although heavy metal-containing buffers were used to reduce the effects of interferents in an ion selective electrode-based assay, the mercury-containing compounds of the prior art now can be avoided, leading to increased assay sensitivity, to increased technician safety and to easier, safer and more economical and environmentally-compatible disposal of the spent metal-free composition.

First, it was shown that the carbonate-sensitive membrane of an ion selective electrode is not desensitized by the borate-containing metal-free composition of Example 1. The composition of Example 1 was compared to a composition including mercury(II) ions complexed with ethylenediaminetetracetic acid (EDTA) in a buffer of [tris(hydroxymethyl)aminoethane] (TRIS) and tetramethylammonium hydroxide (Example 2).

EXAMPLE 2

| Prior Art Metal-Containing Composition | |
|---|---|
| Ingredient | % (by weight) |
| Water, deionized | 98.45 |
| Nonionic Surfactant | 0.05 |
| Tetramethylammonium Hydroxide | 0.50 |
| TRIS Hydrochloride | 0.78 |
| Mercuric Acetate | 0.09 |
| Ethylenediaminetetraacetic Acid | 0.12 |
| Sodium Bicarbonate | 0.01 |
| Total | 100.00 |

The composition of Example 2 (pH-8.55–8.65) was prepared in an essentially identical manner as the composition of Example 1. The metal-free composition of Example 1 and the metal-containing composition of Example 2 were used in the ion selective electrode-based assay of a standardized test sample for carbonate ion. The standardized test sample included:

| Sodium Chloride | 135 mM/L (millimoles per liter), |
|---|---|
| Potassium Chloride | 4 mM/L, and |
| Sodium Bicarbonate | 25 mM/L; |
| to which was added: | |

| -continued | |
|---|---|
| Coumadin | 10 mg/dL (milligrams per deciliter) |
| Potassium Bromide | 10 mM/L |
| Sodium Salicylate | 160 mg/L (milligrams per liter) |
| Sodium Gentisate | 160 mg/L, and |
| Lithium Heparin | 286 USP units/5 ml. |

The ion selective electrode-based assay was performed in the above-described automated system and utilized the ion selective electrode for carbonate ion disclosed in U.S. Pat. No. 4,810,351. TABLE II lists the data observed over a one week period in this comparative test to illustrate the reduction in assay interference provided by a prior art, metal-containing composition (Example 2) and a metal-free composition of the present invention (Example 1).

In these ion selective electrode-based assays standard operating protocols for the TECHNICON RA-1000® automated system were used. For example, the system was etched daily, and the system was calibrated and checked for performance daily. Accordingly, for each of the eight days of the test, the following protocol was performed for each interferent to establish the effect of the interferent on the measured concentration of carbonate ion. The effect of the interferent, in mM/L, on the measurement for carbonate concentration was determined from the results of cups 9 and 10 for each of the five interferents studied.

| Cup Number | Standardized Sample Assayed |
|---|---|
| 1 | Low Calibrator[1] |
| 2 | Low Calibrator |
| 3 | High Calibrator[2] |
| 4 | High Calibrator |
| 5 | Aqueous Control[3] |
| 6 | Aqueous Control |
| 7 | Aqueous Control |
| 8 | Aqueous Control |
| 9 | Interferent[4] |
| 10 | Interferent |
| 11 | Aqueous Control |
| 12 | Aqueous Control |
| 13 | Aqueous Control |
| 14 | Aqueous Control |
| 15 | High Calibrator |
| 16 | High Calibrator |
| 17 | Low Calibrator |
| 18 | Low Calibrator |

[1] Calibrator including a low concentration of bicarbonate ion;
[2] Calibrator including a high concentration of bicarbonate ion;
[3] Aqueous bicarbonate solution having a concentration intermediate to the low and high calibrators; and
[4] Aqueous standardized solution of an interferent added to aqueous bicarbonate solution [3].

TABLE II

Reduction of Effects of Interfering Compounds in Ion Selective Electrode Assays for Carbonate Ion (Example 1 vs. Example 2)

| | EX. 1 | EX. 2 | EX. 1 | EX. 2 |
|---|---|---|---|---|
| | DAY 0 | | DAY 1 | |
| Slope (mv/dec)[1] | 23.3 | 20.4 | 24.2 | 19.8 |
| Coumadin | 0.42 | 0.0 | 0.5 | 0.0 |
| Bromide | 0.7 | 0.4 | 1.3 | 0.6 |
| Salicylate | 1.4 | 2.1 | 1.7 | 3.7 |
| Gentisate | 1.0 | 1.1 | 0.8 | 1.0 |
| Heparin | 0.0 | 0.0 | 0.0 | 0.0 |
| | DAY 2 | | DAY 3 | |
| Slope (mv/dec) | 24.1 | 21.1 | 23.6 | 21.3 |
| Coumadin | 0.3 | 0.0 | 0.7 | 0.0 |
| Bromide | 1.0 | 0.9 | 1.5 | 1.2 |

TABLE II-continued

Reduction of Effects of Interfering Compounds in Ion
Selective Electrode Assays for Carbonate Ion
(Example 1 vs. Example 2)

|  | EX. 1 | EX. 2 | EX. 1 | EX. 2 |
|---|---|---|---|---|
| Salicylate | 2.1 | 4.1 | 2.5 | 4.5* |
| Gentisate | 1.3 | 1.2 | 1.3 | 1.7 |
| Heparin | 0.0 | 0.1 | 0.0 | 0.0 |
|  | DAY 6 | | DAY 7 | |
| Slope (mv/dec) | 22.5 | 20.8 | 23.3 | 20.7 |
| Coumadin | 0.7 | 0.0 | — | 0.0 |
| Bromide | 2.0 | 1.2 | — | 1.2 |
| Salicylate | 4.0 | 5.1* | 4.1 | 4.9* |
| Gentisate | 2.0 | 1.4 | — | 1.7 |
| Heparin | 0.0 | 0.0 | — | 0.0 |

*assay was flagged by the TECHNICON RA-1000 ® to indicate an inadequate signal equilibrium, or therefore a high degree of interference
[1]Millivolts/decade, defined as the slope of the Nernst plot of millivolts vs. the logarithm of carbonate concentration;
[2]Units are in mM/L for each interferent.

The data presented in TABLE II show that the slope observed in assays utilizing the composition of Example 1 remained essentially constant over the one week testing period within the range of 22.5 to 24.2. Accordingly, the membrane of the ion selective electrode is not desensitized by the borate-containing, metal-free composition of Example 1 because the slope of the Nernstian response did not decrease appreciably over the one week period. This essentially constant slope over time is compared to the slopes observed for assays utilizing a mercury-containing composition of the prior art. The slope for these assays also remained essentially constant, ranging from 19.8 mv/dec to 21.3 mv/dec. Accordingly, like the metal-containing compositions of the prior art, the borate-containing, metal-free composition of the present invention does not desensitize the membrane of the ion selective electrode.

Moreover, the metal-free composition of the present invention outperforms the prior art, metal-containing composition in regard to sensitivity of the assay. The absolute size of the observed slope for assays utilizing a composition of the present invention is about 20% greater than the observed slope for assays utilizing the metal-containing composition. Accordingly, a smaller difference in analyte concentration is more accurately measured when a test sample is diluted with a metal-free composition of the present invention because the response (i.e. slope) is greater than the response observed when a prior art metal-containing composition is used to dilute the test sample.

It also should be noticed that the composition of Example 1 reduced the effects of interferents essentially equally as well as the composition of Example 2. In general, carbonate concentrations for each sample were determined. An observed concentration greater than the reference concentration was due to salicylate interference. Any interference, i.e. variation in signal due to an interferent, like sodium salicylate, was reduced to an equivalent additional analytical concentration in mM using standard Nernst relationships. In particular, the observed salicylate interference is less in assays using the borate-containing, metal-free composition of Example 1. For example, two to three days of using the composition of Example 1 are required before salicylate interference (2.1 mM/L at day 2, 2.5 mM/L at day 3) is as high as the salicylate interference observed when using the metal-containing composition of Example 2 on day zero (2.1 mM/L at day 0). Therefore, after using the metal-free composition for six days, the ion selective electrode exhibits a salicylate effect (4.0 mM/L) that is demonstrated after two days of using the mercury-containing composition of the prior art (4.1 mM/L). Coumadin and bromide interferences are slightly higher in assays using the composition of Example 1, but the increases in interference are relatively small.

In this comparative test, it also was observed that equilibration flags, denoted in TABLE II by an asterisk, were not observed when the composition of Example 1 was used in the assay. Generally, interferents, such as salicylate, tend to produce artificially-high carbonate readings and to increase electrode response. The electrode response is automatically monitored in the TECHNICON RA-1000 ® system and is flagged whenever the response of the electrode is significantly increased. This flag detects interference bias for carbonate exceeding a level ranging from 4 mM/L to 7 mM/L. Therefore, the metal-free composition of the present invention further reduced the effects of salicylate ion compared to the prior art metal-containing composition.

Furthermore, it was shown that incorporating a heavy metal complex into the composition of Example 1 did not further reduce the adverse effects of an interferent. TABLE III illustrates the results of assays performed using the composition of Example 1, either absent a metal complex or including a metal complex, on the interfering effects of salicylate on a carbonate-sensitive membrane that has been in use for 7 days. The data in TABLE III demonstrate that adding an ethylenediaminetetraacetate complex of various metals to the composition of Example 1 did not further reduce salicylate interference in a carbonate assay compared to using the composition of Example 1 absent a metal complex. Therefore, surprisingly and unexpectedly, the metal-free composition of Example 1 effectively reduces the effects of interferents, and especially anionic interferents, even in the absence of a metal complex. In contrast, the prior art teaches and requires a metal complex to reduce the effects of interferents. Further, in comparison to assays utilizing a metal-containing buffer composition, the observed slopes for assays using a metal-free composition of the present invention are increased, and therefore provide a more sensitive and accurate assay.

TABLE III

Effect of Heavy Metal-EDTA[1] Complex on Salicylate
Interference in Borate-containing Composition
of Example 1

| | Added Metal Salt | | |
|---|---|---|---|
| | None | None | Mercury(II) Acetate |
| Slope (mv/dec) | 23.3 | 20.3 | 20.5 |
| Salicylate Effect[2] | 4.1 | 4.5 | 3.9 |
| Added Salt | Magnesium Sulfate | Lead(II) Chromate | Copper Acetate |
| Slope (mv/dec) | 23.2 | 17.0 | 21.7 |
| Salicylate Effect[2] | 3.8 | 6.2 | 5.1 |
| Added Salt | Silver Acetate | Cadmium Nitrate | Barium Sulfate |
| Slope (mv/dec) | 19.6 | 5.6[3] | 22.5 |
| Salicylate | 5.0 | 21.6 | 4.1 |

TABLE III-continued

Effect of Heavy Metal-EDTA[1] Complex on Salicylate
Interference in Borate-containing Composition
of Example 1

Effect[2]

[1]Metal concentration - 3 mM/L; EDTA (ethylenediaminetetraacetic acid) concentration-5 mM/L;
[2]Effect on carbon dioxide concentration upon adding 160 mg/L salicylate to 25 mM/L $CO_2$, in mM/L;
[3]Low slope possibly attributed to interference effect of anion.

The data illustrated in TABLE IV demonstrate that as the pH of the composition of Example 1 is increased, the slope of an ion selective electrode membrane used to assay for carbonate ion for 8 days decreases from 24.8 to 20.4 mv/dec. The assay results illustrated in TABLE IV were obtained by the same procedure used to obtain the assay results illustrated in TABLE II. The pH of the metal-free composition of Example 1 was adjusted by adding tetramethylammonium hydroxide to raise the pH or by adding boric acid to lower the pH. It has been theorized that the increased hydroxyl concentration at higher pH values attacks the ionophore in the membrane, and the sensitivity and accuracy of the ion selective electrode therefore is decreased. Accordingly, the pH of the composition of Example 1 should be sufficiently high to convert the various forms of carbon dioxide in the test sample to carbonate ion, i.e. a pH above about 8.2, and sufficiently low to minimize the hydroxide effect, (i.e. a pH below 9.0). Similarly, a suitable pH range for the ion selective electrode-based assay of other predetermined ions can be determined, such that an accurate assay is achieved and such that the useful life of the ion selective electrode membrane is maximized. The inverse relationship between

TABLE IV

Effect of pH of Composition of Example 1
on Life of Membrane

| pH | 8.0 | 8.2 | 8.4 | 8.6 | 8.8 | 9.0 | 9.2 |
|---|---|---|---|---|---|---|---|
| $SCO_2$[1] | 24.8 | 24.4 | 22.7 | 22.8 | 22.2 | 21.6 | 20.4 |
| SK[2] | 45.4 | 37.0 | 46.8 | 35.5 | 48.1 | 48.5 | 45.4 |
| SNa[3] | 59.7 | 58.1 | 58.0 | 55.7 | 58.9 | 59.0 | 59.9 |
| Salicylate Effect[4] | 4.8 | 4.6 | 5.2 | 5.1 | 5.2 | 5.3 | 5.3 |

[1]Slope carbon dioxide assay, in mV/decade;
[2]Slope potassium assay, in mV/decade;
[3]Slope sodium assay, in mV/decade; and
[4]Interfering affect of salicylate on the carbonate assay, in mM/L.

pH and the observed slope was not observed in the potassium and sodium assays. Therefore, the hydroxyl ion content of the metal-free composition does not effect the membrane of the ion selective electrodes used to detect potassium and sodium ions. Overall, the data presented in TABLE IV show that a pH of from about 8.2 to about 8.6 provides an acceptable balance between maximizing the slope of the Nernstian response and the buffering capacity of the metal-free composition. To achieve the full advantage of the present invention, the pH of the metal-free composition used in the assay for carbonate ion is buffered in the range of 8.35 to 8.45.

To show that other buffers in addition to a borate buffer can be included in a metal-free composition of the present invention, TRIS·HCl, replaced the boric acid of Example 1 to provide a composition (Example 3) having a pH of 8.41. The composition of Example 3 also reduced the effects of interferents, like salicylate, but the ion selective electrode-based assay using the composition of Example 3 demonstrated an increasing interference with ionic strength that is related to an increase of chloride ion concentration, and also demonstrated a slope decrease.

Therefore, the above data show that a heavy metal can be removed from the buffer composition used to dilute the test sample and that the interfering effects of various compounds often present in the test sample, like anionic interferents, still are effectively reduced. In accordance with an important feature of the present invention, a borate compound is used to reduce the effects of interfering compounds. In addition, a borate compound, within the suitable pH range, is the preferred buffering agent because chloride ion is absent. Accordingly, in the absence of chloride ion, an ion selective electrode-based assay for chloride ion can be included in the assay sequence. However, outside the pH range that a borate compound acts as a buffer, another suitable buffering agent can be added to the metal-free composition. Furthermore, it is not necessary to add a preservative compound to the metal-free composition because the borate compound is self-preserving.

Therefore, in summary, the metal-free composition of the present invention is a buffering composition that provides significantly higher sensitivity in ion selective electrode-based assays than the prior art compositions, and avoids the use and disposal of a toxic heavy metal containing composition. The present metal-free composition can be adapted for use in other ion selective electrode sensors, such as chloride sensors, in addition to the above-described use in a carbonate sensor. It also has been demonstrated that the metal-free composition substantially reduces the effects of interferents that often are present in test samples. The interfering effects are reduced by the present metal-free composition at least equally as well as the prior art metal-containing reagents. In addition, the present metal-free composition provides improved resistance to the effects of salicylate ion over the prior art compositions.

It also has been demonstrated that a metal-free composition of the present invention can be used as a wash solution in an ion selective electrode-based assay. A wash solution is used both during sampling and during standby periods when the analyzer is not performing assays. By allowing the ion selective electrodes to continuously contact a mixture of the buffer solution and the wash solution, electrode stability and rapid response time is maintained. A typical metal-free wash solution is presented in the composition of Example 4, wherein the sodium bicarbonate, sodium chloride and potassium chloride are included to provide a solution having a concentration of 20 mM/L carbon dioxide, 3.9 mM/L potassium and 120 mM/L sodium.

EXAMPLE 4

Metal-Free Wash Solution

| Ingredient | % (by weight) |
|---|---|
| Boric Acid | 1.64 |
| Tetramethylammonium Hydroxide | 0.52 |
| Sodium Chloride | 0.036 |
| Potassium Chloride | 0.002 |
| Sodium Bicarbonate | 0.024 |
| Nonionic Surfactant[1] | 0.046 |
| Water (deionized) | 97.732 |
| Total | 100.000 |

(pH - 8.35 to 8.45)

[1]TRITON X-100, Rohm & Haas Co., Philadelphia, PA.

To further demonstrate the new and unexpected results achieved by using a metal-free composition of the present invention in the ion selective electrode-based assay of a predetermined ion, the composition of Example 1 was used in the assay of human serum samples for carbonate ion. The data were collected on a TECHNICON RA-1000® automated analyzer utilizing an ion selective electrode module including a carbonate-sensitive ion selective electrode described in U.S. Pat. No. 4,810,351. Fifty hospital serum samples were sampled over a 5-day period. The serum samples were assayed both on a TECHNICON RA-1000® analyzer and a TECHNICON SMAC® analyzer, and the results of the two assays were compared. With the metal-free composition used in the TECHNICON RA-1000® analyzer as the y parameter and a prior art method of analyzing for carbonate ion, i.e. on a TECHNICON SMAC® system, as the x parameter, the assay for sodium ion had a slope (TECHNICON RA-1000® vs. TECHNICON SMAC®) of 0.998 and an intercept of 3.3 mM over a concentration range of 120 to 170 mM; the potassium ion assay had slope of 1.002 with an intercept of 0.08 mM over a concentration range of 2.5 to 17 mM; and carbon dioxide (carbonate) assay had a slope of 1.169 and an intercept of −4.8 mM over a concentration range of 17 to 38 mM.

Figure 2:
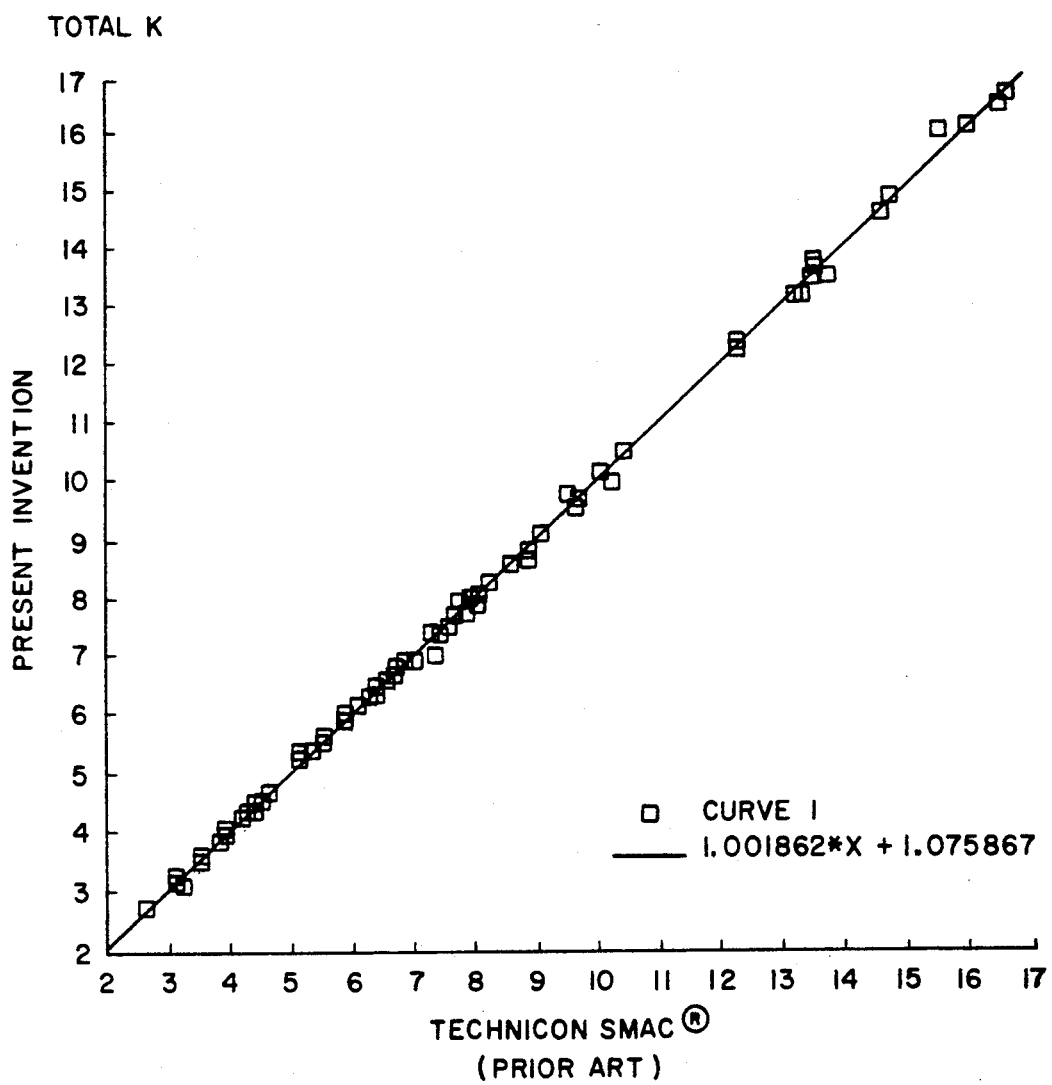
FIGS. 2 and 3 are plots showing the correlation of results of assays for potassium ion and sodium ion, respectively, performed on test samples including either from about 2 mM to about 17 mM potassium ion or from about 120 mM to about 170 mM sodium ion; in each plot, the y-axis plots the assay results obtained from an ion selective electrode-based assay using a metal-free composition of the present invention and the x-axis plots assay results of the same test sample obtained by a prior art method.
Figure 3:
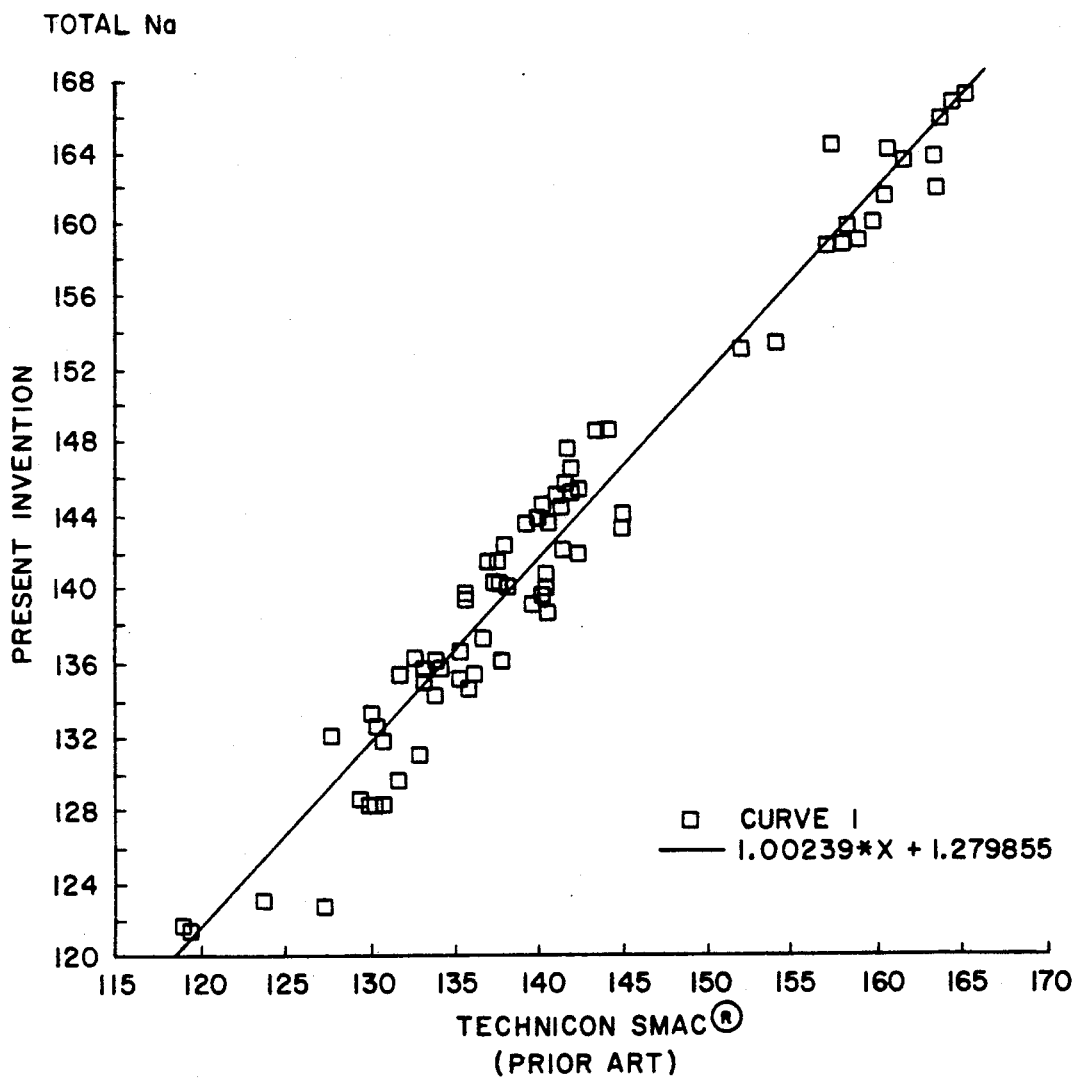

FIGS. 1-3 illustrate another series of assays performed on test samples for total carbon dioxide, potassium ion and sodium ion. Similar to the previous set of assays, the samples were assayed both on a TECHNICON RA-1000® analyzer and a TECHNICON SMAC® analyzer, and the results of the two assays were compared. With the metal-free composition used in the TECHNICON RA-1000® analyzer as the y parameter and a prior art method of analyzing for carbonate ion, i.e. on a TECHNICON SMAC® system, as the x parameter, the assay for total carbon dioxide (FIG. 1) exhibited a slope (TECHNICON RA-1000® vs. TECHNICON SMAC®) of 1.081 over a concentration range of about 16 mM to about 38 mM. FIG. 1 illustrates the excellent correlation of assay results obtained by the composition and method of the present invention to the assay results obtained by a prior art assay method.

The test samples also were assayed for potassium ion and sodium ion concentration. FIGS. 2 and 3 show the excellent correlation of assay results between the method and composition of the present invention and a prior art assay method. In particular, FIG. 2, for potassium ion, shows that, over the concentration range of from about 2 mM to about 17 mM, the graph comparing the present invention to the prior art correlates almost identically because the slope of the graph is 1.002. Similarly, the slope of the plot in FIG. 3 is 1.002, thereby illustrating an excellent correlation between data obtained according to the present invention and data obtained by a prior art assay method for sodium ions over a concentration range of from about 120 mM to about 170 mM.

Over a 7-day period, the slope of a carbon dioxide assay utilizing a metal-containing buffer composition ranged from 19.8 to 21.3 mV/decade, whereas the observed slope in assays using the metal-free buffer composition ranged from 23.6 to 24.2 mV/decade. Corresponding interferences on carbon dioxide assays measured in an aqueous background of 160 mM sodium ion, 4 mM potassium ion and 25 mM bicarbonate ion were (in mmol/L):

TABLE V

Effect of Interferents on $CO_2$ Assay (mM/L)

| Interferent | Concentration of Interferent[1] | Buffer Metal-Containing | Buffer Metal-Free |
|---|---|---|---|
| Salicylate | 16 mg/dL | 2.1[2] | 1.4 |
| Coumadin | 10 mg/dL | 0.0 | 0.4 |
| Bromide | 10 mM/L | 0.4 | 0.7 |
| Gentisate | 16 mg/dL | 1.1 | 1.0 |
| Heparin | 286 USP units/5 ml | 0.0 | 0.0 |
| Salicylate | 16 mg/dL | 4.5 | 2.5 |
| Coumadin | 10 mg/dL | 0.0 | 0.7 |
| Bromide | 10 mM/L | 1.2 | 1.5 |
| Gentisate | 16 mg/dL | 1.7 | 1.3 |
| Heparin | 286 USP units/5 ml | 0.0 | 0.0 |
| Salicylate | 16 mg/dL | 4.9 | 3.0 |
| Coumadin | 10 mg/dL | 0.0 | 0.0 |
| Bromide | 10 mM/L | 1.2 | 0.9 |
| Gentisate | 16 mg/dL | 1.7 | 0.6 |
| Heparin | 286 USP units/5 ml | 0.0 | 0.0 |

[1]Concentration of interferent added to the test sample;
[2]Effect of interferent on measured concentration of carbon dioxide in the test sample, in mM/L.

In another test, the effect of the ionic strength of the heavy metal-free buffering composition on the slope of the Nernstian response and on salicylate interference was determined. TABLE VI illustrates the slope of the carbon dioxide assay and the observed silicylate interference for assays performed over an 8-day period and utilizing borate-containing buffers and wash solutions of the present invention that include 0.3M, 0.1M or 0.05M boric acid. The date in TABLE VI show that the slope is essentially.

TABLE VI

Effect of Ionic Strength of the Metal-Free Buffer on the Slope of the Assay and on Salicylate Interference

| | Day | | | | | | | | |
|---|---|---|---|---|---|---|---|---|---|
| | 0 | 1 | 2 | 3 | 4 | 5 | 6 | 7 | 8 |
| Buffer 0.3M[1] | | | | | | | | | |
| $SCO_2$[2] | -- | 24.3 | -- | -- | -- | -- | -- | -- | 23.7 |
| Salicylate Affect[3] | -- | 2.0 | -- | -- | -- | -- | -- | -- | 4.6 |
| Buffer 0.1M[4] | | | | | | | | | |
| $SCO_2$ | -- | -- | 22.5 | -- | -- | -- | -- | -- | -- |
| Salicylate Effect | -- | -- | 3.3 | -- | -- | -- | -- | -- | -- |
| Buffer 0.05M[5] | | | | | | | | | |
| $SCO_2$ | -- | -- | 23.1 | 22.9 | -- | -- | 22.6 | 22.8 | 22.8 |
| Salicylate Effect | -- | -- | 4.0 | 4.8 | -- | -- | 5.1 | 5.4 | 5.9 |

[1]Metal-free composition of Example 1 including 0.3M boric acid, pH-8.42;
[2]Slope carbon dioxide assay, in mV/decade;
[3]Interfering effect of salicylate on the carbonate assay, in mM/L;
[4]Metal-free composition of Example 1 including 0.1M boric acid, pH-8.47;
[5]Metal-free composition of Example 1 including 0.05M boric acid, pH-8.45.

unchanged over the 8-day period, regardless of the ionic strength of the metal-free buffer. For example, assays utilizing the buffer including 0.3M boric acid exhibited a slope of 24.3 mV/decade at day one and a slope of 23.7 mV/decade at day eight. Similarly, the the assays utilizing the buffer including 0.05M boric acid exhibited an essentially constant slope of 23.1 mV/decade to 22.8 mV/decade from day two through day eight. The data of TABLE VI also show that as the ionic strength increases the interfering salicylate effects decrease, i.e. from 5.9 mM/L for the 0.05M boric acid buffer to 4.6 mM/L for the 0.3M boric acid buffer at day eight, and from 4.0 mM/L for the 0.05M boric acid buffer to 3.3 mM/L for the 0.1M boric acid buffer at day two.

The above examples and test data show that removing the heavy metal from the buffering composition does not adversely affect the assay and that a reduction in assay interference is observed when a borate compound is included in the metal-free buffering composition. In addition, a borate-containing, metal-free composition is self-preserving, does not cause deplating of the reference electrode, and provides a more ideal sodium response. The metal-free composition maintains electrode selectivity for the predetermined analyte of interest; does not attack the membrane of the ion selective electrode and therefore maintains the useful lifetime of the electrode; and produces an essentially heavy metal-free waste product that is safely handled and easy to dispose.

In a direct comparison to the prior art buffering composition utilizing a TRIS buffer and a mercury salt, the present metal-free composition, including a borate compound, provides a better buffering because the borate compound has a greater ionic strength than the TRIS buffer; provides a more accurate assay because the borate-containing composition is not as sensitive to temperature changes as the TRIS-based buffer; does not desensitize the membrane of the ion selective electrode; provides a more sensitive response to sodium ions, potassium ions and, especially, carbonate ions; eliminates the need of a preservative compound that may be incompatible with the ISE; and allows use of the same buffer to assay a single test sample for the other predetermined analytes, e.g. chloride ion.

Obviously, many modifications and variations of the invention as hereinbefore set forth can be made without departing from the spirit and scope thereof and therefore only such limitations should be imposed as are indicated by the appended claims.

I claim:

1. A composition for use in an ion selective electrode-based assay of a test sample for a predetermined analyte selected from the group consisting of carbonate ion, chloride ion, sodium ion, potassium ion and combinations thereof, said composition comprising from about 0.3% to about 5% by weight of a borate compound; from about 0.1% to about 2% by weight of either an alkaline alkalinity adjusting compound selected from the group consisting of ammonium hydroxide, sodium hydroxide, potassium hydroxide, lithium hydroxide, barium hydroxide, magnesium hydroxide, calcium hydroxide, a monalkylammonium hydroxide, a dialkylammonium hydroxide, a trialkylammonium hydroxide, a tetraalkylammonium hydroxide and combinations thereof, wherein the alkyl group includes from one to four carbon atoms, or an acidic alkalinity adjusting compound to provide a suitable pH to assay for the predetermined analyte; an amount up to about 0.5% by weight of a nonionic surfactant; and water, wherein the composition is essentially free of heavy metals, and wherein the borate compound substantially reduces the effects of an anionic interfering compound present in the test sample.

2. The composition of claim 1 wherein the borate compound is present in an amount ranging from about 1% to about 4% by weight of the composition.

3. The composition of claim 1 wherein the borate compound is selected from the group consisting of boric acid, sodium tetraborate and a combination thereof.

4. The composition of claim 1 wherein the acidic alkalinity adjusting compound is selected from the group consisting of hydrochloric acid, phosphoric acid, hydrofluoric acid, sulfuric acid, acetic acid, nitric acid and combinations thereof.

5. The composition of claim 1 having a pH in the range of from 5 to about 11.

6. A composition for use in an ion selective electrode-based assay of a test sample for a predetermined analyte selected from the group consisting of carbonate ion, chloride ion, sodium ion, potassium ion and combinations thereof, said composition comprising from about 0.3% to about 5% by weight of a borate compound; from about 0.1% to about 2% by weight of either an alkaline alkalinity adjusting compound selected from the group consisting of ammonium hydroxide, sodium hydroxide, potassium hydroxide, lithium hydroxide, barium hydroxide, magnesium hydroxide, calcium hydroxide, a monalkylammonium hydroxide, a dialkylammonium hydroxide, a trialkylammonium hydroxide, a tetraalkylammonium hydroxide and combinations thereof, wherein the alkyl group includes from one to four carbon atoms, or an acidic alkalinity adjusting compound to provide a suitable pH to assay for the predetermined analyte; a buffer compound in addition to the borate compound; and water, wherein the composition is essentially free of heavy metals, and wherein the borate compound substantially reduces the effects of an anionic interfering compound present in the test sample.

7. The composition of claim 6 wherein the borate compound is present in an amount ranging from about 1% to about 4% by weight of the composition.

8. The composition of claim 6 wherein the borate compound is selected from the group consisting of boric acid, sodium tetraborate and a combination thereof.

9. The composition of claim 6 wherein the acidic alkalinity adjusting compound is selected from the group consisting of hydrochloric acid, phosphoric acid, hydrofluoric acid, sulfuric acid, acetic acid, nitric acid and combinations thereof.

10. The composition of claim 6 having a pH in the range of from about 5 to about 11.

11. The composition for use in an ion selective electrode-based assay of a test sample for carbonate ion comprising from about 0.3% to about 5.0% by weight of a borate compound; from about 0.1% to about 2% by weight of a tetraalkylammonium hydroxide, wherein the alkyl group includes from one to four carbon atoms to provide a pH in the range of from about 8 to about 9; and water, wherein the composition is essentially free of heavy metals, and wherein the borate compound substantially reduces the effects of an anionic interfering compound in the test sample on the assay.

12. The composition of claim 11 wherein the borate compound is present in an amount ranging from about 1% to about 4% by weight of the composition.

13. The composition of claim 11 wherein the borate compound is present in an amount ranging from about 1.5% to about 3% by weight of the composition.

14. The composition of claim 11 having a pH in the range of from about 8.2 to about 8.6.

15. The composition of claim 11 wherein the borate compound is boric acid and the tetraalkylammonium hydroxide is tetramethylammonium hydroxide.

16. A method of assaying a test sample for a predetermined analyte by an ion selective electrode, whereby the effects of an anionic interfering compound present in the test sample are substantially reduced, comprising:
   a) adding a sufficient amount of a buffer composition to the test sample to provide a suitable buffered pH to assay for the predetermined analyte and to form an assay solution, said buffer composition being essentially free of heavy metals, and said buffer composition comprising:

1) a from about 0.3% to about 5% by weight of borate compound to reduce the effects of the anionic interfering compound and to buffer the test sample;
2) a sufficient amount of an alkalinity adjusting compound to provide a suitable pH to assay for the predetermined analyte;
3) and water; and b) analyzing the assay solution for the predetermined analyte by means of an ion selective electrode capable of sensing the predetermined analyte.

17. The method of claim 16 wherein the borate compound is selected from the group consisting of boric acid, sodium tetraborate and a combination thereof.

18. The method of claim 16 wherein the test sample is a biological fluid.

19. The method of claim 18 wherein the biological fluid is blood plasma, blood serum, cerebrospinal fluid or urine.

20. The method of claim 16 wherein the predetermined analyte is selected from the group consisting of carbonate ion, chloride ion, sodium ion, potassium ion and combinations thereof.

21. The method of claim 16 wherein the predetermined analyte is carbonate ion and the suitable buffered pH is in the range of from about 8 to about 9.

22. The method of claim 21 wherein the borate compound is boric acid and the alkalinity adjusting compound is a tetraalkylammonium hydroxide, wherein the alkyl group includes from one to four carbon atoms.

23. The method of claim 22 wherein the tetraalkylammonium hydroxide is tetramethylammonium hydroxide.

24. The method of claim 16 wherein the buffer composition is capable of reducing the effects of the interfering compound selected from the group consisting of salicylate, gentisate, coumadin, bromide, heparin, ibuprofen and combinations thereof.

25. A method of assaying a test sample for total carbon dioxide concentration, wherein the effects of an anionic interfering compound present in the test sample are substantially reduced, comprising:

a) adding a sufficient amount of a buffer composition to the test sample to adjust the pH of the test sample to a sufficient level to convert a portion of the carbon dioxide present in the test sample in a free form and to convert a portion of the carbon dioxide present in the test sample in a fixed form to carbonate ions and to form an assay solution, said buffer composition being essentially free of heavy metals, and said buffer composition having a pH above 8, and comprising from about 0.3% to about 5% by weight of a borate compound to reduce the effects of the interfering compound and to buffer the test sample, an alkalinity adjusting compound to provide a pH of above 8, and water;

b) analyzing the assay solution by means of an ion selective electrode that is capable of sensing carbonate ions; and c) correlating the ion selective electrode analysis for carbonate ions to the concentration of total carbon dioxide in the test sample.

26. The method of claim 25 wherein the buffer composition is added to the test sample in a volume ratio of from about 5 parts to about 25 parts of the buffer composition to one part of the test sample.

27. The method of claim 25 wherein the buffer composition has a pH in the range of from about 8 to about 9.

28. The method of claim 25 wherein the buffer composition has a pH in the range of from about 8.2 to about 8.6.

29. The method of claim 16 wherein the assay solution has a pH in the range of from about 5 to about 11.

30. The method of claim 16 wherein the assay solution has a pH of less than about 5 or greater than about 11, and wherein the buffer composition further comprises a second buffer compound in addition to the borate compound.

31. A composition for use in an ion selective electrode-based assay of a test sample for a predetermined analyte selected from the group consisting of carbonate ion, chloride ion, sodium ion, potassium ion and combinations thereof, said composition comprising from about 0.3% to about 5% by weight of a borate compound; from about 0.1% to about 2% by weight of either an alkaline alkalinity adjusting compound selected from the group consisting of ammonium hydroxide, sodium hydroxide, potassium hydroxide, lithium hydroxide, barium hydroxide, magnesium hydroxide, calcium hydroxide, a monoalkylammonium hydroxide, a dialkylammonium hydroxide, a trialkylammonium hydroxide, a tetraalkylammonium hydroxide and combinations thereof, wherein the alkyl group includes from one to four carbon atoms, or an acidic alkalinity adjusting compound to provide a suitable pH to assay for the predetermined analyte; a buffer compound in addition to the borate compound; and water, wherein the composition is essentially free of heavy metals and has a pH of less than about 5 or greater than about 11; and wherein the borate compound substantially reduces the effects of an anionic interfering compound present in the test sample.

* * * * *